United States Patent [19]

Takahashi

[11] Patent Number: 5,125,143
[45] Date of Patent: Jun. 30, 1992

[54] DEVICE FOR SECURING SKIN TUBE TO BENDABLE TUBE PORTION OF ENDOSCOPE

[75] Inventor: Nagashige Takahashi, Tokyo, Japan

[73] Assignee: Asahi Kogaku Kogyo Kabushiki Kaisha, Tokyo, Japan

[21] Appl. No.: 552,010

[22] Filed: Jul. 13, 1990

[30] Foreign Application Priority Data

Jul. 19, 1989 [JP] Japan ................... 1-188414

[51] Int. Cl.⁵ .................. B23P 19/04; A61B 1/00
[52] U.S. Cl. ........................ 29/237; 29/446; 29/469.5; 128/4
[58] Field of Search .......... 29/446, 447, 469.5, 29/517, 237, 234, 235, 225; 128/4, 6; 385/118; 600/6, 7; 604/280, 281

[56] References Cited

U.S. PATENT DOCUMENTS

| 283,960 | 8/1883 | Boyd | 29/447 |
|---|---|---|---|
| 4,227,293 | 10/1980 | Taylor | 29/447 |
| 4,427,000 | 1/1984 | Ueda | 128/6 |
| 4,470,415 | 9/1984 | Wozniak | 29/447 |
| 4,944,287 | 7/1990 | Takahashi et al. | 128/4 |

Primary Examiner—Joseph M. Gorski
Assistant Examiner—Peter Dungba Vo
Attorney, Agent, or Firm—Sandler, Greenblum & Bernstein

[57] ABSTRACT

A device for securing a skin tube to a bendable tube portion that is formed at the distal end of the insert part of an endoscope, the bendable tube portion being bendable by remote control. The method of securing a skin tube to a bendable tube portion comprises the steps of: fitting a flexible skin tube over the bendable tube portion; fitting a fitting member into the groove at at least one end portion of the skin tube, the fitting member having a shape which is fittable to the groove; loosely fitting a securing device around the end portion of the skin tube, the securing device being formed from a shape memory material which has previously memorized a shape with which the securing device is capable of peripherally pressing the end portion of the skin tube and, at the same time, pressing the fitting member against the surface of the groove; and restoring the securing device to the memorized shape.

7 Claims, 2 Drawing Sheets

DEVICE FOR SECURING SKIN TUBE TO BENDABLE TUBE PORTION OF ENDOSCOPE

BACKGROUND OF THE INVENTION

1. Field of the Invention

The present invention relates to a method of and device for securing a skin tube to a bendable tube portion that is formed at the distal end of the insert part of an endoscope, the bendable tube portion being bendable by remote control.

2. Description of the Prior Art

The bendable tube portion of an endoscope is generally bent with a small radius of curvature and therefore needs to be covered with a skin tube which is elastic and highly flexible.

According to a typical conventional skin tube securing method, a skin tube is fitted over the bendable tube portion of an endoscope, with an adhesive applied therebetween at two end portions of the skin tube, and then the two end portions of the skin tube are externally tied tight with a thread or the like so that no leakage of water will occur.

Since the insert part of a typical conventional endoscope has a circular cross-section, a skin tube can be readily and surely secured to the bendable tube portion by tying tightly with a thread or the like, as described above.

However, in the case of an endoscope wherein a groove is axially formed in the outer surface of the insert part for the purpose of detachably mounting, for example, a forceps channel tube, a skin tube cannot tightly be tied with a thread due to the presence of the groove and cannot therefore be secured in a watertight manner.

SUMMARY OF THE INVENTION

An object of the present invention is to provide a method of securing a skin tube to a bendable tube portion of an endoscope, which enables a skin tube to be surely and readily secured to a bendable tube portion which has a groove formed in the outer surface thereof.

It is another object of the present invention to provide a skin tube securing device which is effectively usable in the above-described method.

Other objects and advantages of the present invention will become apparent from the following detailed description of an illustrated embodiment of the invention.

According to the present invention, there is provided a method of securing a skin tube to a bendable tube portion of an endoscope which has a groove in the outer surface, comprising the steps of: fitting a flexible skin tube over the bendable tube portion; fitting a fitting member into the groove at least one end portion of the skin tube, the fitting member having a shape which is fittable to the groove; loosely fitting a securing device around the end portion of the skin tube, the securing device being formed from a shape memory material which has previously memorized a shape with which the securing device is capable of peripherally pressing the end portion of the skin tube and, at the same time, pressing the fitting member against the surface of the groove; and restoring the securing device to the memorized shape.

In addition, there is provided a device for securing a skin tube to a bendable tube portion of an endoscope which has a groove in the outer surface, comprising: a fitting member which is fitted into the groove to press one end portion of the skin tube against the surface of the groove; and a securing device which is fitted around the end portion of the skin tube and which has previously memorized a shape with which the securing device is capable of peripherally pressing the end portion of the skin tube and, at the same time, pressing the fitting member against the surface of the groove.

BRIEF DESCRIPTION OF THE DRAWINGS

The present invention may be more fully understood from the description of a preferred embodiment of the invention set forth below, together with the accompanying drawings, in which.

DESCRIPTION OF THE EMBODIMENT

One embodiment of the present invention will be described below with reference to the accompanying drawings.

Figure 1:
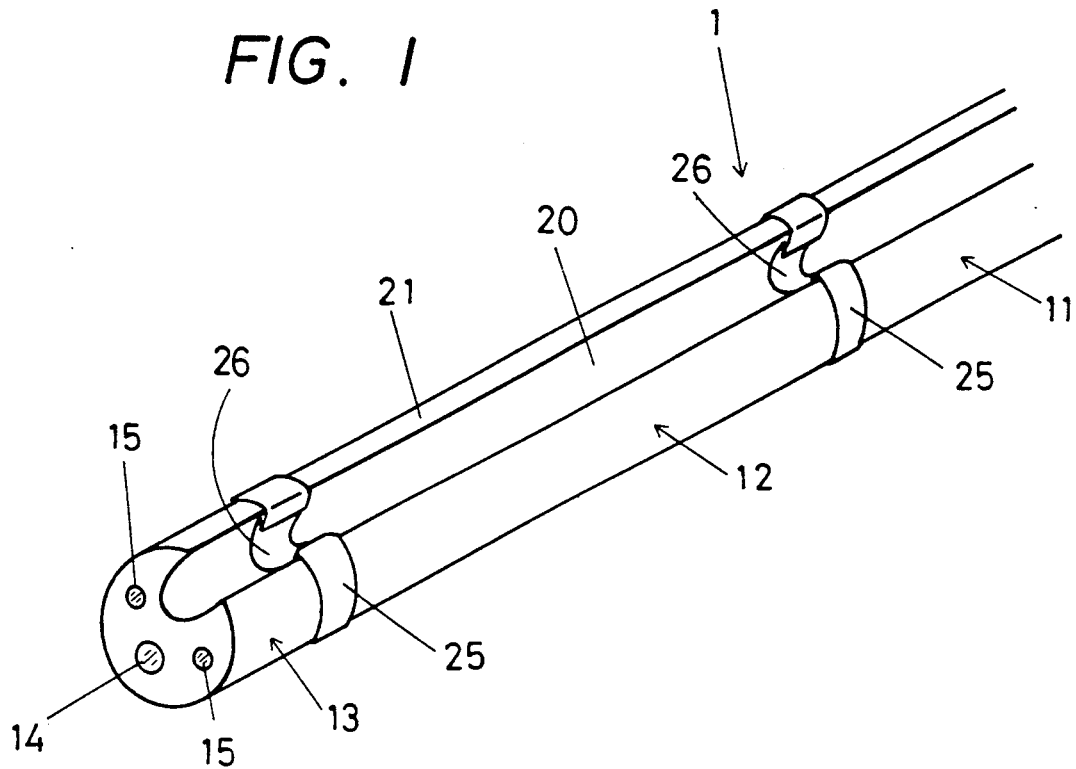
FIG. 1 is a perspective view of an insert part of an endoscope, showing one embodiment of the present invention.

In FIG. 1, reference numeral 1 denotes an insert part of an endoscope. The insert part 1 comprises a flexible tube 11 and a bendable tube portion 12 which is provided at the distal end of the flexible tube 11, the bendable tube portion 12 being bendable by remote control. In addition, a distal end part 13 is connected to the distal end of the bendable tube portion 12. The distal end part 13 incorporates an objective lens (not shown) and has a viewing window 14 that is formed in the outer surface thereof. Reference numeral 15 denotes illuminating windows for illuminating the observation field of view.

A groove 20 which has a U-shaped cross-sectional configuration is axially formed in the outer surface of the insert part 1 over the entire length thereof. When the endoscope is to be used, a detachable forceps channel tube (not shown) is fitted into the U-shaped groove 20.

Reference numeral 21 denotes a skin tube for covering the bendable tube portion 12, which is made of a synthetic rubber material which is elastic and highly flexible.

The skin tube 21 is secured at each end thereof to an inner frame and externally pressed by a securing member 25 and a fitting member 26.

Figure 2:
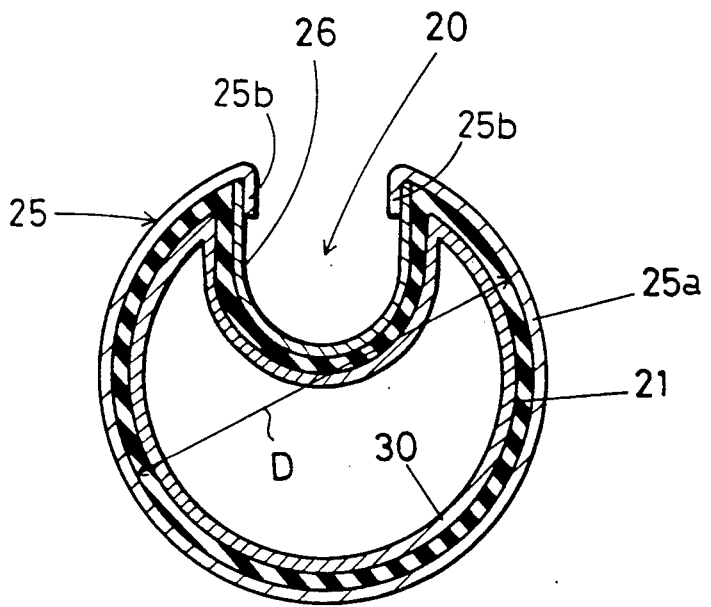
FIG. 2 is a sectional view of a secured portion of a skin tube in one embodiment of the present invention.

FIG. 2 is a sectional view of one end portion of the skin tube 21. Reference numeral 30 denotes an inner metal frame, and 21 the above-described skin tube. The fitting member 26 is formed with a U-shaped cross-section to press an end portion of the skin tube 21 against the surface of the U-shaped groove 20 by being fitted therein. For example, a stainless steel plate may be employed as a constituent material for the fitting member 26.

The securing member 25 is formed from a shape memory alloy which has previously memorized a C-like shape (hereinafter referred to as "C-portion 25a") with two opposing end portions 25b which are bent inwardly. With this memorized shape, the securing member 25 is capable of peripherally pressing an end portion of the skin tube 21 and, at the same time, pressing the fitting member 26 against the surface of the groove 20.

For example, a ribbon of TiNi shape memory alloy may be employed as a constituent material for the securing member 25. The securing member 25 is restored to the memorized shape at ordinary temperature. The use of a thin-walled ribbon makes it possible to minimize the projection on the surface of the insert part of the endoscope.

FIG. 2 shows the securing member 25 which is restored to the memorized shape. The C-portion 25a fixedly presses the outer periphery of the skin tube 21, and the two end portions 25b fixedly press the fitting member 26 into the U-shaped groove 20.

Figure 3A:
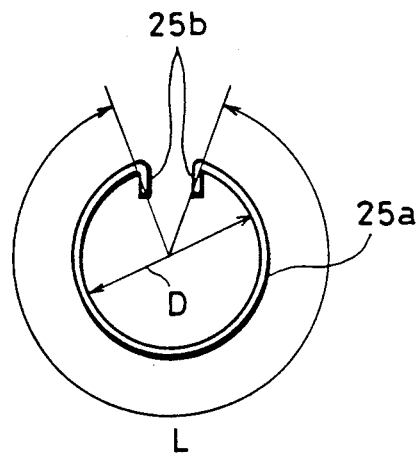
FIGS. 3a and 3b are front views of a securing member which is employed in one embodiment of the present invention.
Figure 3B:
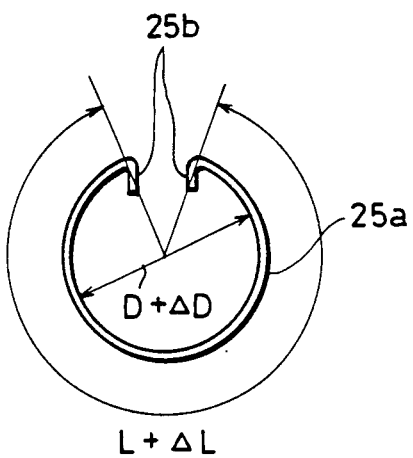

FIG. 3a and 3b show the change in the shape of the securing member 25.

FIG. 3a shows the way in which the securing member 25 is made to memorize a shape. The length L and diameter D of the C-portion 25a are set to dimensions with which the securing member 25, when set in the securing position that is shown in FIG. 2, slightly crushes the skin tube 21. Then, the securing member 25 is subjected to a heat treatment at a predetermined transformation temperature, thereby conducting a shape-memory treatment.

Next, the securing member 25 is drawn so that a strain of about 5 to 7% is generated, at a temperature below the Af point (the temperature at which the inverse transformation from the martensite phase to the mother phase terminates). As a result, the length of the C-portion 25a increases to L+ΔL, and the diameter also increases to D+ΔD, as shown in FIG. 3b. Accordingly, in this state the securing member 25 can readily be fitted to the bendable tube portion 12. When stored as a part, the securing member 25 is held at, for example, around −50° C., to maintain this shape.

After the securing member 25, which is in the above-described state, is fitted to the bendable tube portion 12, the temperature is raised to a level at which the securing member 25 is restored to the memorized shape (for example, it is heated at about ordinary or room temperature). In consequence, the securing member 25 is restored to the original shape, which is shown in FIG. 3a. By virtue of the shrinkage of the securing member 25 at this time, the skin tube 21 is peripherally pressed and fastened, thereby being secured, together with the fitting member 26.

Figure 4A:
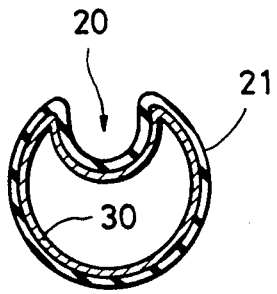
FIGS. 4a to 4c are sectional views showing the process of securing a skin tube according to one embodiment of the present invention.
Figure 4B:
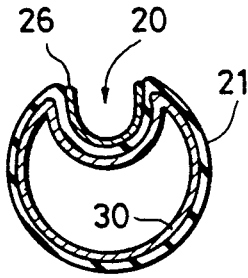
Figure 4C:
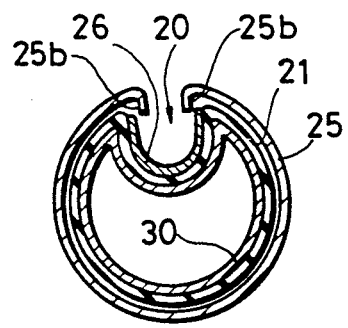

FIGS. 4a to 4c show sequentially the steps of the method of securing a skin tube to a bendable tube portion of an endoscope, according to the present invention.

First, the skin tube 21 is fitted over the bendable tube portion 12 of the endoscope, as shown in FIG. 4a. An adhesive is applied in between the metal frame 30 and the skin tube 21 at the two end portions of the skin tube 21.

Next, the fitting member 26 is fitted into the U-shaped groove 20 at each end of the skin tube 21, as shown in FIG. 4b. It should be noted that the skin tube 21 may be secured by the method of the present invention only at one end thereof and secured at the other end by another method.

Then, the securing member 25, which has been stored at low temperature, is fitted in such a manner that the two end portions 25b face the U-shaped groove 20, as shown in FIG. 4c. The securing member 25 is loosely fitted around the end portion of the skin tube 21.

Next, the securing member 25 is heated to a temperature at which it is restored to the original shape, which has been memorized. As a result, the C-portion 25a of the securing member 25 peripherally presses the skin tube 21 and the two end portions 25b press the fitting member 26 against the surface of the U-shaped groove 20, thereby fastening the skin tube 21 tight, as shown in FIG. 2.

If an adhesive is also applied between the fitting member 26 and the securing member 25, on the one hand, and the skin tube 21, on the other, stronger securing force is obtained.

According to the present invention, a skin tube can be surely and readily secured to even a bendable tube portion of an endoscope which has a groove in the outer surface, without any damage to the skin tube.

While the invention has been described by reference to a specific embodiment chosen for purposes of illustration, it should be apparent that numerous modifications could be made thereto by those skilled in the art without departing from the basic concept and scope of the invention. For example, elastic material can be used instead of the shape memory alloy.

I claim:

1. A device for securing a skin tube to a bendable tube portion of an endoscope, said endoscope having a groove in an outer surface, said skin tube being positioned over the outer surface of said bendable tube portion of the endoscope, said device comprising:

a fitting member which is fitted into said groove in said bendable tube portion to press one end portion of said skin tube against an outer surface of said groove; and securing means which is fitted around said end portion of said skin tube, said securing means having a previously memorized shape with which said securing means is capable of peripherally pressing said end portion of said skin tube and, at the same time, pressing said fitting member against the outer surface of said groove.

2. A skin tube securing device according to claim 1 wherein said groove has a U-shaped cross-sectional configuration, and said fitting member has a U-shaped configuration which is conformable to said groove.

3. A skin tube securing device according to claim 1, wherein said securing means memorizes a C-like shape with two opposing end portions which are bent inwardly.

4. A skin tube securing device according to claim 1, wherein said securing means is restored to said memorized shape at ordinary temperature.

5. A skin tube securing device according to claim 1, wherein said securing means is formed from a shape memory alloy.

6. A skin tube securing device according to claim 5, wherein said shape memory alloy is a TiNi shape memory alloy.

7. A device for securing a skin tube to an insert part of an endoscope, said insert part having a groove in an outer surface, said skin tube being positioned over said insert part, said device comprising:

a fitting member which is fitted into said groove of said insert part to press one end portion of said skin tube against an outer surface of said groove; and securing means which is fitted around said end portion of said skin tube, said securing means being capable of peripherally pressing said end portion of said skin tube and, at the same time, pressing said fitting member against the outer surface of said groove.

* * * * *